(12) United States Patent
Norstedt et al.

(10) Patent No.: US 6,773,919 B2
(45) Date of Patent: Aug. 10, 2004

(54) EXPRESSION VECTOR FOR PRODUCTION OF RECOMBINANT PROTEINS

(75) Inventors: Gunnar Norstedt, Bromma (SE); Tim Wood, Stockholm (SE); Daniel Sliva, Stockholm (SE); Bertil Enberg, Grödinge (SE); Peter Lobie, Bandhagen (SE); Lars-Arne Haldosen, Rönninge (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 08/963,288

(22) Filed: Nov. 3, 1997

(65) Prior Publication Data

US 2003/0192064 A1 Oct. 9, 2003

Related U.S. Application Data

(63) Continuation of application No. PCT/SE95/01235, filed on Oct. 19, 1995.

(30) Foreign Application Priority Data

Oct. 21, 1994 (SE) ............................................... 9403613

(51) Int. Cl.$^7$ .......................... C07H 21/04; C12N 5/00; C12N 15/00; C12N 15/09; C12N 15/63
(52) U.S. Cl. .................... 435/455; 435/320.1; 435/325; 536/24.1
(58) Field of Search .............................. 435/320.1, 325, 435/455; 536/24.1, 23.1; 800/4, 7, 13, 14, 18

(56) References Cited

U.S. PATENT DOCUMENTS 5,814,517 A * 9/1998 Seidel et al. ................ 435/325

FOREIGN PATENT DOCUMENTS

| EP | 0420055 | 4/1991 |
|----|---------|--------|
| WO | WO 8801648 | 3/1988 |
| WO | WO 9405796 | 3/1994 |

OTHER PUBLICATIONS

Lindquester et al. Avian tropomyosin gene expression. Nucleic Acids Research 17(5): 2099–2118, 1989.*

Le Stunff et al. Contrasting acute in vivo nuclear actions of growth hormone and prolactin. Molec. and Cell. Endocrinology 121:109–117, 1996.*

Petitclerc et al. The effect of various introns and transcription terminators on the efficiency of expression vectors in various cultured cell lines and in the mammary gland of transgenic mic. J. of Biotechnol. 40:169–178, 1995.*

Sliva et al. Growth hormone specifically regulates serine protease inhibitor gene transcription via gamma–activated sequence–like DNA elements. J. Biol. Chem. 269(42):26208–26214, 10/94.*

Wall, RJ Transgenic livestock: Progress and prospects for the future. Theriogenology 45:57–68, 1996.*

Yoon et al. An inducible nuclear factor binds to a growth hormone–regulated gene. J. Biol. Chem. 265(32):19947–19954, 11/90.*

Lavenu et al. The cis–acting elements known to regulate c–myc expression ex vivo are not sufficient for correct transcription in vivo. Oncogene 9:527–536, 1994.*

Yoon et al, *The Journal of Biological Chemistry*, 262(9):4284–4289 (Mar. 25, 1987).

Dialog MedLine Abstract, Dialog Accession No. 06192046, MedLine Accession No. 87166046, Yoon et al, *J. Biol. Chem*, 262 (9), pp. 4284–4289, (1987).

LeCama et al, *J. Biol. Chem.*, 260(34):21532–21539 (1994).

Enberg et al, *J. Mol. Endocrinol.*, 12(81):39–46 (Feb. 1994).

Goujon et al, *Proc. Natl. Acad. Sci, USA*, 91:957–961 (Feb. 1994).

* cited by examiner

*Primary Examiner*—Anne-Marie Falk
(74) *Attorney, Agent, or Firm*—Fish & Richardson P.C.

(57) ABSTRACT

A method of enhancing the transcription of a gene in a DNA construct incorporated into the genome of a eucaryotic host cell, wherein the DNA construct comprises a structural gene for a desired protein or polypeptide in a gene promoter upstream of the structural gene, comprises providing at least one enhancer element comprising the nucleotide sequence TTC TGA GAA upstream of the promoter, and exposing the DNA construct to lactogenic stimuli. An expression vector, a host cell and a transgenic mammal containing the vector are of interest.

40 Claims, No Drawings

EXPRESSION VECTOR FOR PRODUCTION OF RECOMBINANT PROTEINS

The present application is a continuation of International Application No. PCT/SE95/01235 filed Oct. 19, 1995, assigned U.S. Ser. No. 08/809,256.

FIELD OF THE INVENTION

The present invention relates to DNA plasmids to be used for the production of recombinant proteins. More specifically, the present invention concerns the addition of specific DNA elements to expression plasmids that serve a function as enhancing elements. The outcome is to improve the yields of recombinant protein production.

BACKGROUND OF THE INVENTION

There are a number of different strategies for the large-scale production of recombinant proteins to be used in, for example, the pharmaceutical industry. In certain cases it is desirable that the recombinant protein is made in eucaryotic hosts. These hosts may be cultivated cells or animals made transgenic with respect to the gene of interest. In the latter situation, transgenic expression in milk is a valuable technique since transgenes, active in the mammary gland, have been described and milk is a readily available body fluid.

The present invention relates to, in an unrestricted way, an improvement in expression vectors used to produce recombinant proteins in milk. These improved expression vectors will increase the yield of valuable recombinant proteins which will be of value for the facilitation of subsequent handling and purification steps.

Construction of a transgene requires certain basic ingredients, one being the structural gene containing the coding information for the protein of interest. A basal eucaryotic gene expression promoter is also required. In addition, other sequences can be used that confer tissue specificity or enhance expression in response to stimulus. The present invention relates to a specific type of enhancers, namely enhancers responding to hormonal stimuli. The particular enhancer in question is a sequence of DNA that confers a response to signals evoked by pituitary hormones belonging to the group of lactogenic hormones such as prolactin (Prl) and placenta lactogen (PL) and somatogenic hormones such as growth hormone (GH). Both of these groups of hormones occupy central roles in the stimulation of mammary gland development and function. The present invention concerns the definition of enhancers responding to both lactogenic and somatogenic hormones and the construction of expression vectors, that, in their ability to respond to both lactogenic and somatogenic hormones, will function in an improved manner as transgenes for production of recombinant proteins in milk.

Previous studies have defined a gene, the Serine Protease Inhibitor 2.1 (SPI) gene, that responds to GH. In the 5' flank of this gene a DNA element has been identified that enhances gene expression in a GH-dependent fashion. The sequence of this GH response element (SPI GH-RE) in question is: SEQ ID NO:1 GATCTACGCTTCTACTAATC-CATGTTCTGAGAAATCATC CAGTCTGCCCATG, (Yoon et al. J. Biol. Chem. 265; 19947 (1991)) Within this sequence we now disclose a shorter "SPI-GAS like element"; TTCTGAGAA, that constitutes the core GH regulated sequence. As exemplified below the SPI-GAS element is also functional when transferred to a reporter gene such as the Luciferase gene (Sliva D. et al J. Biol.. Chem. in press). In the following we also disclose that the GH-regulated sequences described above are also regulated by prolactin and that this can be used to design new expression vectors that improve existing vectors used to produce recombinant proteins in milk.

EXAMPLES

Example 1
Identification of a Core GH Regulated Sequence

The 50 bp SPI-GHRB SEQ ID NO:1; (GATCTACGCTTCTACTAATCCATGTTCT GAGAAATCATCCAGTCTGCCCATG) was used to identify a core GH regulated sequence using gel electrophoresis mobility shift assay (GEMSA). Nuclear extracts were prepared and incubated with a 32P labelled 50 bp SPI-GHRE. Subsequently the extracts were analysed on polyacrylamide gels. The results showed that nuclear proteins, dependent on GH, bound to this DNA sequence. By competition with shorter oligonucleotides derived from SPI-GHRE a core GH sequence was identified. Based on certain sequence homologies to interferon response elements we called this sequence SPI-GAS and also demonstrated that SPI-GAS functions as a GE regulated DNA element when put into a reporter vector. The core SPI-GAS has the following sequence; TTCTGAGAA.

Example 2
Prolactin and Growth Hormone both Activate SPI-TK Reporter Gene.

An expression plasmid containing a recombinant hormone responsive reporter consisting of six repeats of a 50 bp growth hormone responsive element (GH-RE) from the serine protease inhibitor (SPI) 2.1 promoter fused to the thymidine kinase (TK) promoter was constructed. Corresponding constructs were made using the SPI-GAS element Variants expressing either the bacterial protein chloramphenicol acetyl transferase (CAT) or firefly luciferase (SFI-CAT or SPI-Luc respectively) cDNAs were then constructed. Techniques to make these vectors are well known to experts in the fluid. The plasmid DNA constructions were transfected, together with plasmid expression vectors encoding either rat growth hormone receptors or mouse prolactin receptors, into Chinese hamster ovary (CHO), (CHO), COS, and Buffalo rat liver (BRL) cells. using DOTAP liposomes and according to the manufacturer instructions. Cells were incubated overnight with DNA and DOTAP in serum free media, left and then exposed to growth hormone or prolactin for 12 hours. Cell lysates were then prepared and CAT or luciferase enzyme activity measured. Both growth hormone and prolactin treatment lead to an approximately 5-fold stimulation reporter enzyme expression relative to transfected but non-hormone treated cells. These results show that both growth hormone and prolactin can regulate the reporter construct and that a requisite for this is the presence of SPI elements. The core element in the SPI-TK-reporter gene that confers GH regulation is likely to be; TTCTGAGAA, and similar results can be obtained with this element termed SPI-GLE as with the longer, 50 bp element named SPI-GHRE.

Example 3
Multimeric SPI Elements in Front of a TK Promoter Give a Better Response.

Reporters plasmids containing one to six copies of the 50 bp SPI element fused to the TK promoter were constructed. The growth hormone responsiveness of these constructs was tested by transfection into a CHO cell line that stably expresses the rat growth hormone receptor DNA. Growth hormone stimulation of these cells showed that multimerization of SPI elements resulted in a larger growth hormone response.

Example 4
Expression of Stable Incorporated SPI-TK-Luciferase is Growth Hormone Regulated.

To demonstrate that SPI elements retain growth hormone responsiveness function when genomically integrated CHO cells were transfected with the three following plasmids: SPI-LUC (described in example 1), an expression vector containing the CMV promoter and rat growth hormone receptor cDNA and a neomycin expression vector. Neomycin resistant clones were tested for growth hormone response by exposing cells to growth hormone for 12 h under serum free conditions and then measuring luciferase activity in cell lysates. The results indicated a three-fold growth hormone-regulated induction of expression of the stably integrated reporter gene.

Example 5
SPI Elements in Front of a Strong Promoter (SV40) Results in a Protein Production that is Further Enhanced by GH.

Six copies of the SPI element were introduced upstream of a strong CMV promoter driving expression of the CAT cDNA in a plasmid construct. This construct was transfected into CHO-4 cells and GH regulation was tested as described above. It was found that GH stimulated the production of CAT.

What is claimed is:

1. An vitro method of enhancing the transcription of a gene in a DNA construct when the DNA construct is incorporated into the genome of a eukaryotic host cell, the method comprising:
 (a) providing a DNA construct comprising a structural gene for a desired protein or polypeptide, a gene promoter upstream of and operably linked to the structural gene, and six copies of an enhancer element upstream of the promoter;
 (b) transfecting the eukaryotic host cell to incorporate the DNA construct into the genome of the host cell; and
 (c) exposing the DNA construct in the eukaryotic host cell to a hormone selected from the group consisting of lactogenic hormones, somatogenic hormones and mixtures thereof;
 wherein the enhancer element comprises the nucleotide sequence TTCTGAGAA, with the proviso that the nucleotide sequence does not contain the DNA sequence of nucleotide sequence SEQ ID NO:1, and wherein the enhancer element is responsive to both lactogenic hormones and somatogenic hormones.

2. The method according to claim 1, wherein the enhancer element consists essentially of the nucleotide sequence TTCTGAGAA.

3. An expression vector comprising a structural gene encoding a desired protein or polypeptide and a promoter, wherein the vector further comprises six enhancer elements, and further wherein each of the enhancer elements consists essentially of the nucleotide sequence SEQ ID NO:1.

4. An expression vector according to claim 3, wherein the promoter is a thiamine kinase promoter.

5. An expression vector comprising a structural gene encoding a desired protein or polypeptide and a promoter, wherein the vector further comprises six enhancer elements, and further wherein each of the enhancer elements consists essentially of the nucleotide sequence TTCTGAGAA.

6. An isolated eukaryotic host cell containing the expression vector according to claim 3.

7. An isolated eukaryotic host cell containing the expression vector according to claim 4.

8. An isolated eukaryotic host cell containing the expression vector according to claim 5.

9. An in vitro method of enhancing the transcription of a gene in a DNA construct, the method comprising:
 (a) providing a first DNA construct comprising a structural gene and a promoter upstream of the structural gene,
 (b) incorporating the nucleotide sequence consisting of TTCTGAGAA into the first DNA construct upstream of the promoter, thereby producing a second DNA construct,
 (c) transfecting a eukaryotic host cell to incorporate the second DNA construct into the genome of the host cell; and
 (d) exposing the second DNA construct in the eukaryotic host cell to a hormone selected from the group consisting of lactogenic hormones, somatogenic hormones and mixtures thereof.

10. A method according to claim 9, wherein the hormone is selected from the group consisting of growth hormone, prolactin, placenta lactogen and mixtures thereof.

11. A method according to claim 10, wherein the hormone is selected from the group consisting of prolactin, placenta lactogen and mixtures thereof.

12. An in vitro method of enhancing the transcription of a gene in a DNA construct comprising a structural gene, a promoter upstream of the structural gene, and at least one enhancer upstream of the promoter; the method comprising placing the DNA construct in an environment wherein transcription can occur; and exposing the DNA construct to a hormone selected from the group consisting of lactogenic hormones, somatogenic hormones and mixtures thereof;

wherein the enhancer element consists essentially of the nucleotide sequence TTCTGAGAA.

13. A method according to claim 12, wherein the hormone is selected from the group consisting of growth hormone, prolactin, placenta lactogen and mixtures thereof.

14. A method according to claim 13, wherein the hormone is selected from the group consisting of prolactin, placenta lactogen and mixtures thereof.

15. A method according to claim 1, wherein the hormone is selected from the group consisting of growth hormone, prolactin, placenta lactogen and mixtures thereof.

16. A method according to claim 15, wherein the hormone is prolactin.

17. An in vitro method of enhancing transcription of a structural gene, comprising the steps of:
(a) preparing a plasmid DNA construct comprising a structural gene, a promoter upstream of the structural gene, and at least one enhancer consisting of the sequence TTCTGAGAA upstream of the promoter;
(b) transfecting a cell with the plasmid DNA construct; and
(c) exposing the cell to prolactin.

18. An in vitro method according to claim 17, wherein the plasmid DNA comprises up to six enhancers.

19. An isolated DNA construct comprising a promoter operably linked to a structural gene downstream from said promoter, and six repeats of an enhancer element upstream from said promoter, wherein the enhancer element consists essentially of the sequence TTCTGAGAA.

20. An isolated DNA construct according to claim 19, wherein the enhancer consists of the sequence TTCTGAGAA.

21. An in vitro method of enhancing the transcription of a gene, the method comprising the steps of:
(a) providing a DNA construct comprising the gene, a promoter upstream of the gene, and at least one copy of the nucleotide sequence TTCTGAGAA upstream of the promoter;
(b) transfecting the cell with the DNA construct, and
(e) exposing the DNA construct to prolactin.

22. An in vitro method according to claim 21, wherein the DNA comprises multiple copies of the nucleotide sequence TTCTGAGAA.

23. An in vitro method according to claim 22, wherein the DNA construct comprises six copies of the nucleotide sequence TTCTGAGAA.

24. An in vitro method according to claim 12, wherein the transfecting step comprises transfecting the eukaryotic cell with a plasmid comprising the DNA construct.

25. The method according to claim 2, wherein the enhancer element consists of the nucleotide sequence TTCTGAGAA.

26. An in vitro method of enhancing transcription of a nucleotide sequence, the method comprising:
providing a eukaryotic cell comprising an expression vector comprising (i) a nucleotide sequence encoding a desired protein, (ii) a promoter upstream of the nucleotide sequence, and (iii) an element upstream of the promoter comprising the sequence TTCTGAGAA; and contacting the cell with a lactogenic hormone, thereby enhancing transcription of the nucleotide sequence.

27. The method of claim 26, wherein the lactogenic hormone is prolactin.

28. The method of claim 26, wherein the element comprises the sequence GATCTACGCTTCTACTAATCCATGTTCTGAGAAATCATCCAGTCTGCCCATG (SEQ ID NO:1).

29. The method of claim 26, wherein the element comprises six copies of the sequence TTCTGAGAA.

30. The method of claim 26, wherein the element comprises six copies of the sequence GATCTACGCTTCTACTAATCCATGTTCTGAGAAATCATCCAGTCTGCCCATG (SEQ ID NO:1).

31. An in vitro method of enhancing transcription of a nucleotide sequence, the method comprising:
providing an expression vector comprising (i) a nucleotide sequence encoding a desired protein, (ii) a promoter upstream of the nucleotide sequence, and (iii) an element upstream of the promoter comprising the sequence TTCTGAGAA;

transfecting a eukaryotic cell with the expression vector, and contacting the cell with a lactogenic hormone, thereby enhancing transcription of the nucleotide sequence.

32. The method of claim 31, wherein the lactogenic hormone is prolactin.

33. The method of claim 31, wherein the element comprises the sequence GATCTACGCTTCTACTAATCCATGTTCTGAAATCATCCAGTCTGCCCATG (SEQ ID NO:1).

34. The method of claim 31, wherein the element comprises six copies of the sequence TTCTGAGAA.

35. The method of claim 31, wherein the element comprises six copies of the sequence GATCTACGCTTCTACTAATCCATGTTCTGAGAAATCATCCAGTCTGCCCATG (SEQ ID NO:1).

36. An in vitro method of enhancing transcription of a nucleotide sequence, the method comprising:
constructing an expression vector comprising (i) a nucleotide sequence encoding a desired protein, (ii) a promoter upstream of the nucleotide sequence, and (iii) an element upstream of the promoter comprising the sequence TTCTGAGAA transfecting a eucaryotic cell with the expression vector; and contacting the cell with a lactogenic hormone, thereby enhancing transcription of the nucleotide sequence.

37. The method of claim 36, wherein the lactogenic hormone is prolactin.

38. The method of claim 36, wherein the element comprises the sequence GATCTACGCTTCTACTAATCCATGTTCTGAGAAATCATCCAGTCTGCCCATG (SEQ ID NO:1).

39. The method of claim 36, wherein the element comprises six copies of the sequence TTCTGAGAA.

40. The method of claim 36, wherein the element comprises six copies of the sequence GATCTACGCTTCTACTAATCCATGTTCTGAGAAATCATCCAGTCTGCCCATG (SEQ ID NO:1).

* * * * *

UNITED STATES PATENT AND TRADEMARK OFFICE
CERTIFICATE OF CORRECTION

PATENT NO. : 6,773,919 B2
DATED : August 10, 2004
INVENTOR(S) : Gunnar Norstedt et al.

It is certified that error appears in the above-identified patent and that said Letters Patent is hereby corrected as shown below:

Title page,
Item [56], References Cited, OTHER PUBLICATIONS, "Petitclerc et al.," reference, replace "mic" with -- mice --

Column 6,
Line 31, replace "GATCTACGCTTCTACTAATCCATGTTCTGAAATCATCCAGTCTGCCCATG" with -- GATCTACGCTTCTACTAATCCATGTTCTGAGAAATCATCCAGTCTGCCCATG --

Signed and Sealed this

Twelfth Day of July, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Growth
      Hormone Response Element SPI GH-RE

<400> SEQUENCE: 1
gatctacgct tctactaatc catgttctga gaaatcatcc agtctgccca tg             52